United States Patent [19]

Znaiden et al.

[11] Patent Number: 5,853,741
[45] Date of Patent: *Dec. 29, 1998

[54] VITAMIN C DELIVERY SYSTEM

[75] Inventors: Alexander Paul Znaiden, Trumbull; Brian Andrew Crotty, Branford; Anthony Johnson, Fairfield, all of Conn.

[73] Assignee: Chesebrough-Pond's USA Co., Division of Conopco, Inc., Greenwich, Conn.

[ * ] Notice: The term of this patent shall not extend beyond the expiration date of Pat. No. 5,750,123.

[21] Appl. No.: 696,305

[22] Filed: Aug. 13, 1996

Related U.S. Application Data

[60] Provisional application No. 60/022,509, Jun. 28, 1996.

[51] Int. Cl.$^6$ ....................................... A61K 7/48
[52] U.S. Cl. ...................... 424/401; 424/78.02; 514/474; 514/844
[58] Field of Search ................................ 424/401, 78.02; 514/474, 844

[56] References Cited

U.S. PATENT DOCUMENTS

| | | | |
|---|---|---|---|
| 4,372,874 | 2/1983 | Modrovich | 430/176 |
| 4,720,353 | 1/1988 | Bell | 252/309 |
| 4,742,142 | 5/1988 | Shimizu et al. | 424/401 |
| 4,818,521 | 4/1989 | Tamabuchi | 424/62 |
| 4,869,897 | 9/1989 | Chatterjee et al. | 424/47 |
| 4,980,167 | 12/1990 | Harashima et al. | 424/401 |
| 4,983,382 | 1/1991 | Wilmott et al. | 424/62 |
| 5,078,989 | 1/1992 | Ando et al. | 424/62 |
| 5,137,723 | 8/1992 | Yamamoto et al. | 424/400 |
| 5,140,043 | 8/1992 | Darr et al. | 514/474 |
| 5,266,321 | 11/1993 | Shukuzaki et al. | 424/401 |
| 5,387,417 | 2/1995 | Rentsch | 424/401 |
| 5,605,694 | 2/1997 | Nadaud et al. | 424/401 |
| 5,629,004 | 5/1997 | Candau et al. | 424/401 |
| 5,654,362 | 8/1997 | Schulz, Jr. et al. | 524/862 |

FOREIGN PATENT DOCUMENTS

| | | |
|---|---|---|
| 0 295 886 | 12/1988 | European Pat. Off. . |
| 2 715 844 | 8/1995 | France . |
| 44-22312 | 9/1969 | Japan . |
| 4261111 | 9/1992 | Japan . |
| 1161289 | 6/1968 | United Kingdom . |
| 0 669 126 | 8/1995 | United Kingdom . |
| 96/18374 | 6/1996 | WIPO . |

*Primary Examiner*—Jyothsna Venkat
*Attorney, Agent, or Firm*—Milton L. Honig

[57] ABSTRACT

A cosmetic composition is provided which includes ascorbic acid (Vitamin C) solubilized by a crosslinked non-emulsifying siloxane elastomer in a carrier medium of a volatile siloxane. Aesthetic properties are also improved by the presence of the crosslinked non-emulsifying siloxane elastomer.

4 Claims, No Drawings

VITAMIN C DELIVERY SYSTEM

This application claims the benefit of a U.S. Provisional Application 60/022,509 filed Jun. 28, 1996, now abandoned.

BACKGROUND OF THE INVENTION

1. Field of the Invention

The invention relates to a cosmetic product that can stably store ascorbic acid and then deliver same to the skin.

2. The Related Art

Ascorbic acid, also known by its common name of Vitamin C, has long been recognized as an active substance benefiting skin appearance. Vitamin C reportedly increases the production of collagen in human skin tissue. Wrinkles and fine lines are thereby reduced. An overall healthier and younger-looking appearance results. Vitamin C has also found utility as an ultraviolet ray blocking or absorbing agent. Whitening or bleaching skin compositions have also employed Vitamin C utilizing its property of interference with the melanin formation process. There also is a belief that ascorbic acid interacts with the human immune system to reduce sensitivity to skin aggravating chemicals. Reduced levels of Vitamin C concentration on the skin have also been implicated with an increase in stress. From all of the foregoing perspectives, Vitamin C or ascorbic acid may provide significant benefit when topically applied.

Unfortunately, Vitamin C is a very unstable substance. Although it is readily soluble in water, rapid oxidation occurs in aqueous media. Solubility of ascorbic acid has been reported to be relatively poor in nonaqueous media, thereby preventing an anhydrous system from achieving any significant level of active concentration. A system is necessary for dissolving or at least uniformly suspending Vitamin C which is also chemically compatible with the active.

The art has sought to overcome the problem in a variety of ways. One approach is the preparation of ascorbic acid derivatives. These derivatives have greater stability than the parent compound and, through biotransformation or chemical hydrolysis, can at the point of use be converted to the parent acid. For instance, U.S. Pat. No. 5,137,723 (Yamamoto et al) and U.S. Pat. No. 5,078,989 (Ando et al) provide glycosylate and ester derivatives, respectively.

U.S. Pat. No. 4,818,521 (Tamabuchi) describes under the background technology a so-called two-pack type cosmetic wherein Vitamin C powder and other ingredients are separately packaged in different containers with mixing just prior to use of the cosmetic. The mixing procedure and expensive packaging were said to be drawbacks of this system. The patent suggests stable oil-in-water type emulsions that are weakly acidic and wherein ascorbic acid has been premixed with a stabilizing oil.

Maintenance of pH below about 3.5 has also been suggested in U.S. Pat. No. 5,140,043 (Darr et al) as a stabilization means for aqueous compositions of ascorbic acid.

Water compatible alcohols such as propylene glycol, polypropylene glycol and glycerol have been suggested as co-carriers alongside water to improve stability. An illustration of this approach can be found in U.S. Pat. No. 4,983,382 (Wilmott and Znaiden). Therein a blend of water and water-miscible organic solvent are combined as a stabilizing system. At least about 40% of the organic solvent must be ethanol while the remainder may be selected from such alcohols as propylene glycol, glycerin, dipropylene glycol and polypropylene glycol.

Japanese Patent 44-22312 (Shionogi) describes the stabilization of Vitamin C in a mainly aqueous medium by a variety of glycols. These include polyethylene glycol, ethylene glycol, diethylene glycol and even ethanol. These formulations are intended for ingestion.

U.S. Pat. No. 4,372,874 (Modrovich) has reported incorporation of relatively large amounts of ascorbic acid in a polar water-miscible organic solvent such as dimethyl sulfoxide. Levels of water are kept below 0.5% through addition of a particulate desiccant to the carrier. Although highly polar systems such as dimethyl sulfoxide may be effective, this and related carriers are toxicologically questionable.

Accordingly, it is an object of the present invention to provide a delivery system for ascorbic acid in which the compound is soluble or at least uniformly dispersible and oxidatably storage stable.

Another object of the present invention is to provide a delivery system which assists the penetration of ascorbic acid into the human skin while avoiding irritation thereof.

Still another object of the present invention is to provide a system for delivering ascorbic acid that is aesthetically pleasing and imparts a soft and smooth skinfeel.

These and other objects of the present invention will become more readily apparent through the following summary, detailed discussion and Examples.

SUMMARY OF THE INVENTION

A cosmetic composition is provided that includes:

(i) from 0.001 to 50% of ascorbic acid;
(ii) from 0.1 to 30% of a crosslinked non-emulsifying siloxane elastomer; and
(iii) from 10 to 80% of a volatile siloxane.

DETAILED DESCRIPTION OF THE INVENTION

Now it has been discovered that ascorbic acid can be stabilized against decomposition and also stably suspended in a system containing a crosslinked non-emulsifying siloxane elastomer and a volatile siloxane. Although not wishing to be bound by any theory, it is considered that the elastomer provides a three-dimensional structure which prevents Vitamin C from precipitating from either water or oil phases. Moreover, the three-dimensional structure allows the amount of water to be minimized thereby minimizing ascorbic acid oxidation.

Ascorbic acid is available from several sources including Roche Chemicals. Amounts of this material may range from 0.001 to 50%, preferably from 0.1 to 10%, optimally from 1 to 10% by weight.

Crosslinked non-emulsifying siloxane elastomers of this invention will have an average number molecular weight in excess of 10,000, preferably in excess of 1,000,000 and optimally will range from 10,000 to 20 million. The term "non-emulsifying" defines a siloxane from which polyoxyalkylene units are absent. Illustrative of the elastomer is a material with the CTFA name of Crosslinked Stearyl Methyl-Dimethyl Siloxane Copolymer, available as Gransil SR-CYC (25–35% active elastomer) from Grant Industries, Inc., Elmwood Park, N.J. Supply of related elastomer may also be available from the General Electric Company.

Amounts of the elastomer may range from 0.1 to 30%, preferably from 1 to 15%, optimally from 3 to 10% by weight.

A third essential element of the present invention is that of a volatile siloxane. Illustrative of this category are the cyclo polydimethyl siloxane fluids of the formula $((CH_3)$ $_2SiO))_x$, wherein x denotes an integer of from 3 to 6. The cyclic siloxanes will have a boiling point of less than 250° C. and a viscosity at 25° C. of less than 10 centipoise. Cyclomethicone is the common name of such materials. The tetramer and pentamer cyclomethicones are commercially available as DC 244 and DC 344 from the Dow Corning Corporation.

Amounts of the volatile siloxane will range from 10 to 80%, preferably from 20 to 70%, optimally from 30 to 65% by weight.

Compositions of this invention may further include a pharmaceutically acceptable carrier. Generally the carrier will be an ingredient which can solubilize Vitamin C and all other elements of the composition. Amounts of the carrier may range from 1 to 70%, preferably from 10 to 60%, optimally from 20 to 50% by weight.

Pharmaceutically acceptable carriers may be selected from water, polyols, silicone fluids, esters and mixtures thereof. When present, water may range from 0.5 to 20%, preferably from 1 to 10%, usually from 2 to 6%, optimally less than 5% by weight of the composition.

Advantageously one or more polyols are present as carriers in the compositions of this invention. Illustrative are propylene glycol, dipropylene glycol, polypropylene glycol, polyethylene glycol, sorbitol, hydroxypropyl sorbitol, hexylene glycol, 1,3-butylene glycol, 1,2,6-hexanetriol, glycerin, ethoxylated glycerin, propoxylated glycerin and mixtures thereof. Most preferably the polyol is a mixture of polyethylene glycol, molecular weight ranging from 200 to 2,000, and propylene glycol. Preferred weight ratios of polyethylene glycol to propylene glycol range from 5:1 to 1:10, preferably from 2:1 to 1:5, optimally 1:1 to 1:2. Amounts of the polyol may range from 1 to 50%, preferably from 10 to 40%, optimally from 25 to 35% by weight of the composition.

Silicone oils may also be included as carriers in the compositions of this invention. These oils will be nonvolatile. The nonvolatile silicone oils useful in the compositions of this invention are exemplified by the polyalkyl siloxanes, polyalklyaryl siloxanes and polyether siloxane copolymers. The essentially nonvolatile polyalkyl siloxanes useful herein include, for example, polydimethyl siloxanes with viscosities of from about 5 to about 100,000 centistokes at 25° C. Such polyalkyl siloxanes include the Viscasil series (sold by General Electric Company) and the Dow Corning 200 series (sold by Dow Corning Corporation). Polyalkylaryl siloxanes include poly(methylphenyl)siloxanes having viscosities of from about 15 to about 65 centistokes at 25° C. These are available, for example, as SF 1075 methylphenyl fluid (sold by General Electric Company) and 556 Cosmetic Grade Fluid (sold by Dow Corning Corporation). Useful polyether siloxane copolymers include, for example, a polyoxyalkylene ether copolymer having a viscosity of about 1200 to 1500 centistokes at 25° C. Such a fluid is available as SF-1066 organosilicone surfactant (sold by General Electric Company). Cetyl dimethicone copolyol and cetyl dimethicone are especially preferred because these materials also function as emulsifiers and emollients. The former material is available from Goldschmidt AG under the trademark Abil EM-90. Amounts of the nonvolatile siloxane may range from 0.1 to 40%, preferably from 0.5 to 25% by weight of the composition.

Esters may also be incorporated into the cosmetic compositions as pharmaceutically acceptable carriers. Amounts may range from 0.1 to 50% by weight of the composition. Among the esters are:

(1) Alkyl esters of fatty acids having 10 to 20 carbon atoms. Methyl, isopropyl, and butyl esters of fatty acids are useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate. Particularly preferred are $C_{12}$–$C_{15}$ alcohol benzoate esters.

(2) Alkenyl esters of fatty acids having 10 to 20 carbon atoms. Examples thereof include oleyl myristate, oleyl stearate, and oleyl oleate.

(3) Ether-esters such as fatty acid esters of ethoxylated fatty alcohols.

(4) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(5) Wax esters such as beeswax, spermaceti, myristyl myristate, stearyl stearate.

(6) Sterols esters, of which cholesterol fatty acid esters are examples thereof.

Minor adjunct ingredients may also be included in cosmetic compositions of this invention. These ingredients may be selected from preservatives, fragrances, anti-foam agents, opacifiers, colorants and mixtures thereof, each in their effective amounts to accomplish their respective functions.

The following examples will more fully illustrate the embodiments of this invention. All parts, percentages and proportions referred to herein and in the appended claims are by weight unless otherwise indicated.

EXAMPLE 1

The effect of a crosslinked non-emulsifying siloxane polymer was evaluated in contrast to related siloxanes with respect to suspension/uniform distribution of Vitamin C and resistance to oxidation under storage conditions. Formulations and test results are outlined under Table I.

TABLE I

| | Example No. (Weight %) | | | |
| --- | --- | --- | --- | --- |
| | 1A | 1B | 1C | 1D |
| COMPONENT | | | | |
| Cyclomethicone | 55.5 | 60.0 | 55.5 | 55.5 |
| Polyethylene Glycol 200 | 20.25 | 20.25 | 20.25 | 20.25 |
| Water | 14.0 | 14.0 | 14.0 | 14.0 |
| Ascorbic Acid | 5.0 | 5.0 | 5.0 | 5.0 |
| EM-90 (Cetyl Dimethicone Copolyol) | 0.75 | 0.75 | 0.75 | 0.75 |
| Gransil SR CYL (% Elastomer Active) | 4.5 | — | — | — |
| DC 200 Fluid (Polydimethylsiloxane) | — | — | 4.5 | — |
| Gransurf 671 (Ethoxylated Dimethicone Copolyol) | — | — | — | 4.5 |
| Results | | | | |

TABLE I-continued

| | Example No. (Weight %) | | | |
|---|---|---|---|---|
| | 1A | 1B | 1C | 1D |
| Ascorbic Acid Retention (%) | | | | |
| 2 weeks at RT | 98.6 | Phase separation | Phase separation | Phase separation |
| 2 weeks at 110° C. | 97.8 | | | |
| 4 weeks at 110° C. | 87.9 | | | |

Formulation 1A was a homogeneous stable aesthetically pleasing emulsion of cream-like consistency which retained Vitamin C unoxidized for at least two weeks both at room temperature and at 110° C. By contrast, formulations 1B, 1C and 1D did not form a stable emulsion. These formulations separated and therefore did not uniformly suspend ascorbic acid.

EXAMPLES 2–5

A series of further examples were prepared. Their compositions are outlined under Table II. These formulations provide good storage stability for the ascorbic acid and are aesthetically consumer acceptable.

TABLE II

| | Example No. (Weight %) | | | |
|---|---|---|---|---|
| COMPONENT | 2 | 3 | 4 | 5 |
| Cyclomethicone | 42.0 | 41.6 | 40.0 | 42.0 |
| Gransil SR CYL | 18.0 | 17.9 | 17.3 | 18.0 |
| Propylene Glycol | 16.8 | 14.8 | 17.5 | 15.0 |
| Polyethylene Glycol 200 | 11.0 | 13.7 | 13.5 | 13.5 |
| Ascorbic Acid | 5.0 | 5.0 | 5.0 | 5.0 |
| Dimethyl Isosorbide | 2.0 | 2.0 | 2.0 | 2.0 |
| Cetyl Dimethicone Copolyol | 0.8 | 0.8 | 0.8 | 0.8 |
| Water | balance | balance | balance | balance |

EXAMPLES 6–12

These series of Examples illustrate the scope of the present invention. Various concentrations of ascorbic acid, cyclomethicone and siloxane elastomer are illustrated.

TABLE III

| | Example No. (Weight %) | | | | | | |
|---|---|---|---|---|---|---|---|
| COMPONENT | 6 | 7 | 8 | 9 | 10 | 11 | 12 |
| Cyclomethicone | 36.0 | 36.0 | 36.0 | 40.0 | 40.0 | 45.0 | 32.0 |
| Gransil SR CYL | 24.0 | 24.0 | 24.0 | 20.0 | 20.0 | 15.0 | 27.0 |
| Butylene Glycol | 17.5 | — | 17.5 | — | — | — | 29.0 |
| Glycerin | — | 17.5 | — | — | — | — | — |
| Polyethylene Glycol 200 | 10.0 | — | — | 17.5 | 12.0 | 10.0 | 10.0 |
| Polyethylene Glycol 800 | — | 10.0 | 10.0 | 10.0 | 12.0 | 10.0 | — |
| Dimethyl Isosorbide | 2.0 | 2.0 | 2.0 | 4.0 | 5.0 | 10.0 | 1.0 |
| Ascorbic Acid | 1.0 | 1.0 | 1.0 | 4.0 | 4.0 | 5.0 | 0.5 |
| Cetyl Dimethicone Copolyol | 0.8 | 0.8 | 0.8 | 0.8 | 0.8 | — | — |
| Water | bal. | bal. | bal. | bal. | bal. | bal. | bal. |

The foregoing description and Examples illustrate selected embodiments of the present invention. In light thereof variations and modifications will be suggested to one skilled in the art, all of which are within the spirit and purview of this invention.

What is claimed is:

1. A cosmetic composition comprising:
   (i) from 1 to 10% of ascorbic acid;
   (ii) from 1 to 15% by weight of a crosslinked non-emulsifying siloxane elastomer formed from a divinyl monomer reacting with the Si-H linkages of a siloxane backbone; and
   (iii) from 10 to 80% of a volatile siloxane.

2. The composition according to claim 1 wherein the volatile siloxane is cyclomethicone.

3. The composition according to claim 1 wherein the crosslinked non-emulsifying siloxane elastomer is present in an amount from 3 to 10%.

4. The composition according to claim 1 wherein the volatile siloxane is present in an amount from 20 to 70%.

* * * * *